United States Patent
Brucato et al.

(10) Patent No.: US 10,086,346 B2
(45) Date of Patent: Oct. 2, 2018

(54) PLANT FOR WASTE DISPOSAL AND ASSOCIATED METHOD

(71) Applicant: Archimede S.r.l., Caltanissetta (IT)

(72) Inventors: Alberto Brucato, Caltanissetta (IT); Giuseppe Caputo, Caltanissetta (IT); Franco Grisafi, Caltanissetta (IT); Francesca Scargiali, Caltanissetta (IT); Gianluca Tumminelli, Caltanissetta (IT); Gaetano Tuzzolino, Caltanissetta (IT); Roberto D'Agostino, Caltanissetta (IT); Roberto Rizzo, Caltanissetta (IT)

(73) Assignee: ARCHIMEDE S.R.L., Caltanissetta (IT)

( * ) Notice: Subject to any disclaimer, the term of this patent is extended or adjusted under 35 U.S.C. 154(b) by 0 days.

(21) Appl. No.: 15/565,336

(22) PCT Filed: Apr. 11, 2016

(86) PCT No.: PCT/IB2016/052044
§ 371 (c)(1),
(2) Date: Oct. 9, 2017

(87) PCT Pub. No.: WO2016/166650
PCT Pub. Date: Oct. 20, 2016

(65) Prior Publication Data
US 2018/0117561 A1   May 3, 2018

(30) Foreign Application Priority Data

Apr. 13, 2015 (IT) .................. 102015000011686

(51) Int. Cl.
*B01J 3/00* (2006.01)
*C10J 3/78* (2006.01)
(Continued)

(52) U.S. Cl.
CPC ............... *B01J 3/008* (2013.01); *A61L 11/00* (2013.01); *B01D 19/0073* (2013.01);
(Continued)

(58) Field of Classification Search
CPC ... B01J 3/008; B01J 3/0053; B01J 4/00; B01J 4/001; C02F 11/086; C02F 2303/10;
(Continued)

(56) References Cited

U.S. PATENT DOCUMENTS 4,898,107 A   2/1990   Dickinson

FOREIGN PATENT DOCUMENTS

CN   1868915 A   11/2006
CN   102502943 A   6/2012
(Continued)

OTHER PUBLICATIONS

Patent Cooperation Treaty, Notification of Transmittal of the International Search Report and the Written Opinion of the International Searching Authority, or the Declaration for PCT/IB2016/052044 dated Jul. 6, 2016 10 pages.
(Continued)

*Primary Examiner* — Lessanework Seifu
(74) *Attorney, Agent, or Firm* — Heslin Rothenberg Farley & Mesiti P.C.; Victor A. Cardona, Esq.

(57) ABSTRACT

A plant for the disposal of wastes includes a supercritical water oxidation reactor, a supercritical water gasification reactor, and a feeding system configured for feeding at least two organic currents of wastes to the supercritical water oxidation reactor and supercritical water gasification reactor and configured for feeding at least one aqueous flow within said plant. The feeding system is configured for feeding the at least one aqueous current with a series flow through the supercritical water oxidation reactor and supercritical water gasification reactor. The feeding system is configured for
(Continued)

feeding the at least two organic currents of wastes with a parallel flow through the supercritical water oxidation reactor and supercritical water gasification reactor and so as to selectively feed each of the organic currents of wastes to the supercritical water oxidation reactor or to the supercritical water gasification reactor.

19 Claims, 4 Drawing Sheets (51) Int. Cl.
| | |
|---|---|
| C02F 11/00 | (2006.01) |
| A61L 11/00 | (2006.01) |
| B09B 3/00 | (2006.01) |
| C02F 11/08 | (2006.01) |
| C10J 3/00 | (2006.01) |
| B01D 19/00 | (2006.01) |
| B01J 19/00 | (2006.01) |
| C10J 3/86 | (2006.01) |
| F28D 1/02 | (2006.01) |
| C02F 101/20 | (2006.01) |
| C02F 101/30 | (2006.01) |
| C02F 101/32 | (2006.01) |
| C02F 103/00 | (2006.01) |
| C02F 103/06 | (2006.01) |
| C02F 103/10 | (2006.01) |
| C02F 103/24 | (2006.01) |
| C02F 103/28 | (2006.01) |
| C02F 101/10 | (2006.01) |

(52) U.S. Cl.
CPC .............. *B01J 19/0053* (2013.01); *B09B 3/00* (2013.01); *C02F 11/086* (2013.01); *C10J 3/00* (2013.01); *C10J 3/78* (2013.01); *C10J 3/86* (2013.01); *F28D 1/0226* (2013.01); *C02F 2101/101* (2013.01); *C02F 2101/20* (2013.01); *C02F 2101/301* (2013.01); *C02F 2101/306* (2013.01); *C02F 2101/32* (2013.01); *C02F 2103/002* (2013.01); *C02F 2103/008* (2013.01); *C02F 2103/06* (2013.01); *C02F 2103/10* (2013.01); *C02F 2103/24* (2013.01); *C02F 2103/28* (2013.01); *C02F 2303/10* (2013.01); *C10J 2300/0979* (2013.01); *H05K 999/99* (2013.01); *Y02W 10/30* (2015.05)

(58) Field of Classification Search
CPC ........ C10J 2300/0946; C10J 2300/0979; C10J 2300/1807
See application file for complete search history.

(56) References Cited

FOREIGN PATENT DOCUMENTS

| | | |
|---|---|---|
| GB | 2492070 A | 12/2012 |
| WO | 03/000602 A1 | 1/2003 |

OTHER PUBLICATIONS

Qian et al., "Treatment of sewage sludge in supercritical water and evaluation of the combined process of supercritical water gasification and oxidation," 2015, pp. 218-224, Bioresource Technology.

PLANT FOR WASTE DISPOSAL AND ASSOCIATED METHOD

CROSS REFERENCE TO RELATED APPLICATIONS

This application is a national stage filing under section 371 of International Application No. PCT/IB20106/052044, filed on Apr. 11, 2016, published in English on Oct. 20, 2016, as WO2016/166650 A1 and which claims priority to Italian Application No. 102015000011686 filed on Apr. 13, 2015, the entire disclosure of these applications being hereby incorporated herein by reference.

FIELD OF THE INVENTION

The present invention relates to a waste-disposal plant and to a corresponding disposal method, characterized by high energy efficiency. The present invention has moreover been developed with particular reference to plants in which, in addition to disposal, recovery of the disposed waste is envisaged, with simultaneous production of biofuels and conversion of energy for external use.

PRIOR ART AND GENERAL TECHNICAL PROBLEM

Disposal of waste is so far basically provided in a way specific for the type of waste treated. In particular, for given types of waste that is dangerous for the environment and human health it is necessary to envisage separate treatment plants provided with systems for after-treatment of the reaction products that will enable release into the atmosphere of just harmless species.

A technology consolidated in the sector is that of incinerators, which, however, are affected by limits of performance due to the substantial impossibility of reaching complete and optimal combustion of the waste.

In particular, combustion of the waste in an industrial incinerator always gives rise to reaction products containing partially reacted species, notwithstanding all the measures adopted to favour exposure of the waste to the combustion air on account of the intrinsic inefficiency of this mode of waste treatment. The result is hence a flow of reaction products that contains many dangerous species, which may require a rather complex after-treatment system (which is also characterized by operating limits, as is obvious).

In addition to the aforesaid operating limits, incinerators are also characterized by a low value of the ratio between mass of treated waste and recoverable energy. In other words, the possibility of converting energy flows otherwise dispersed by the incinerator into further energy that can be used elsewhere is extremely low as compared to the amount of waste entering the incinerator.

To overcome these limits, a major part of the activity of research in the sector has concentrated on the development of alternative waste-disposal systems. An example of alternative technologies for treatment and disposal of waste is constituted by supercritical-water gasification (SCWG) and by supercritical-water oxidation (SCWO). The two technologies are in general used individually in various treatment plants (i.e., either supercritical-water gasification or supercritical-water oxidation is used) even though recently some proposals have been made for combination of these technologies.

In particular, a proposal for a waste-disposal plant that combines supercritical-water gasification and supercritical-water oxidation is illustrated in the paper by Qian, et al., "Treatment of sewage sludge in supercritical water and evaluation of the combined process of supercritical water gasification and oxidation", Bioresource Technology, 176 (2015) 218-224.

The document focuses on the use of a plant including an SCWO reactor and an SCWG reactor, where the SCWO reactor is used for treatment of just the liquid phase leaving the gasification reactor, which is contaminated by by-products of the SCWG reaction in the SCWG reactor.

The latter is configured for disposal of sludge containing organic material in low quantities, such as for example sludge from plants for depuration of residential, commercial, or industrial waste water.

However, this plant and the corresponding method for disposal of waste prove to be very costly from an energy standpoint in so far as there is an extremely low conversion of the energy inherent in the waste disposed of into energy that can be used elsewhere. In particular, the process is characterized by an extremely low production of biofuels per unit mass of incoming waste, and hence is characterized by a poor yield in recovery, understood as valorization of the treated waste for production of energy and/or high-quality synthesis products (biofuels).

Furthermore, the type of waste to which the aforesaid document refers is strictly limited to depuration sludges. The scheme and characteristics of the plant described therein are such as to render substantially impracticable treatment of a vast range of waste that is not gasifiable or has a low gasification yield, such as organic waste with high molecular weight, whether liquid or solid (pesticides, pharmaceuticals, heavy and bituminous oils, pet-coke, macromolecules and polymers, etc.), where this is due both to the type and to the intrinsic characteristics of the pollutant agent or agents (physical state, molecular weight, concentration, etc.) and to technological limits deriving from clogging and occlusion of the reactor that render the process discontinuous as a result of the need for continuous interventions of cleaning and descaling of the equipment and of the reactor itself.

Basically, the purpose of the plant described in the document by Qian, et al., is to dispose of the incoming waste by carrying out a gasification at low temperature, thus obtaining a fuel with a methane concentration that is higher than the one that can be obtained with the treatment of pure supercritical-water gasification at high temperature, which, however, would ensure formation of fewer reaction by-products.

The provision of the supercritical-water oxidation reactor at the end of the gasification process enables in fact reduction of the working temperatures in the gasification reactor, increasing the methane yield, even though the total yield is lower than a supercritical-water gasification carried out at higher temperatures.

The supercritical water-oxidation unit consequently has the sole purpose of destroying the organic compounds that have not been gasified on account of the lower temperature of the gasification unit. This method, however, does not prevent the methane produced from being polluted by traces of other hydrocarbons and by hydrogen in amounts such as to not to enable introduction thereof into the grid.

Furthermore, the yield in terms of waste recovery—understood as the ratio between the mass flow rate of the synthesis gas at output and the mass flow rate of the waste at input—is low, as is likewise the energy efficiency of the process in terms of ratio between the lower calorific value of the output synthesis gas per unit mass of the treated waste, and the energy expended per unit input mass of the treated waste necessary for sustaining the process (consumption of traditional fossil fuel or thermal energy supplied to the system as a whole).

OBJECT OF THE INVENTION

The object of the present invention is to overcome the technical problems mentioned previously.

In particular, the object of the invention is to provide a plant for disposal of waste and to provide a corresponding method for disposal of waste that will enable undifferentiated treatment of organic waste of various nature and in different physical states (solid, liquid, gaseous, multiphase mixtures, etc.), irrespective of the danger of the waste itself, at the same time obtaining an extremely high energy efficiency with minimal environmental impact. In the second place, the object of the present invention is to provide a plant (and a corresponding method) in which, in addition to disposal of waste, there is envisaged a recovery of the waste itself, with an energy efficiency and a yield in terms of recovery and valorization of the waste that are extremely high with minimal environmental impact.

SUMMARY OF THE INVENTION

The object of the present invention is achieved by a plant for waste disposal and a method for waste disposal having the features forming the subject of the ensuing claims, which form an integral part of the technical disclosure herein provided in relation to the invention.

In particular, the object of the invention is achieved by a plant for the disposal of wastes including:
  a supercritical water oxidation reactor,
  a supercritical water gasification reactor,
  a feeding system configured for feeding at least two organic currents of wastes to said supercritical water oxidation reactor and supercritical water gasification reactor and configured for feeding at least one aqueous flow within said plant,
  wherein said feeding system is configured for feeding said at least one aqueous current with a series flow through said supercritical water oxidation reactor and supercritical water gasification reactor and
  wherein said feeding system is furthermore configured for feeding said at least two organic currents of wastes with a parallel flow through said supercritical water oxidation reactor and supercritical water gasification reactor and so as to selectively feed each of said organic currents of wastes to said supercritical water oxidation reactor or to said supercritical water gasification reactor.

The object of the invention is moreover achieved by a method for the disposal of wastes in a plant for waste disposal including:
  a supercritical water oxidation reactor,
  a supercritical water gasification reactor,
  a feeding system of currents of wastes configured for feeding at least two organic currents of wastes to said supercritical water oxidation reactor and supercritical water gasification reactor and for feeding at least one aqueous current within said plant,
  the method comprising the steps of:
  feeding, by means of said feeding system, said at least two organics currents of wastes with a parallel flow through said supercritical water oxidation reactor and supercritical water gasification reactor and so as to selectively send each of said organic currents of wastes to said supercritical water oxidation reactor or to said supercritical water gasification reactor,
  feeding, by means of said feeding system, said at least one aqueous current with a series flow through said supercritical water gasification reactor and supercritical water oxidation reactor.

DETAILED DESCRIPTION

Figure 1:
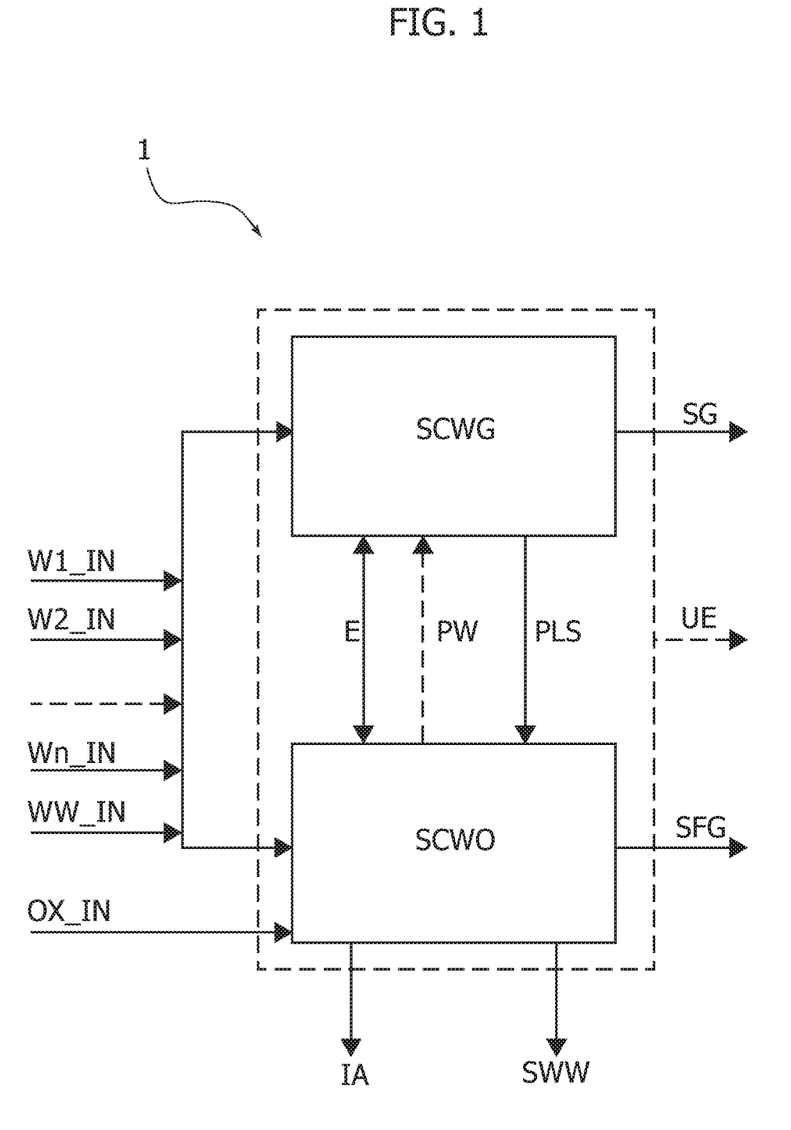
FIG. 1 illustrates a principle diagram of a plant and a method according to various embodiments of the invention.

With reference to FIG. 1, a waste-disposal plant and a corresponding disposal method according to various embodiments of the invention may represented schematically as illustrated here. In this connection, the reference number 1 designates as a whole the diagram of FIG. 1, which can be deemed equivalent both for the waste-disposal plant and for the waste-disposal method according to the invention.

In particular, the plant 1 includes a supercritical-water gasification reactor, designated by the reference SCWG, a supercritical-water oxidation reactor, designated by the reference SCWO, and a feeding system, which is able to feed to the plant 1 at least one aqueous current and at least two organic currents of waste. It should be noted that, for the purposes of the present description, by the term "feeding system" is meant a set of devices capable of feeding the waste at input to the plant 1 but also within the plant 1 itself, where by the term "waste" is in turn meant any compound or chemical species entering the plant 1 or circulating therein that requires treatment before it can leave the plant 1.

It should moreover be noted that the phrase "at least two organic currents" is meant to comprise not only the situations in which two (or more) effectively distinct organic currents are fed to the plant 1, but also the case where just one current containing organic compounds is fed simultaneously (in parallel) to the two reactors SCWG and SCWO (in effect creating two organic currents) in order to generate in the oxidation reactor SCWO the thermal energy necessary to gasify the fraction (generally the majority fraction) fed to the gasification reactor SCWG.

Figure 2:
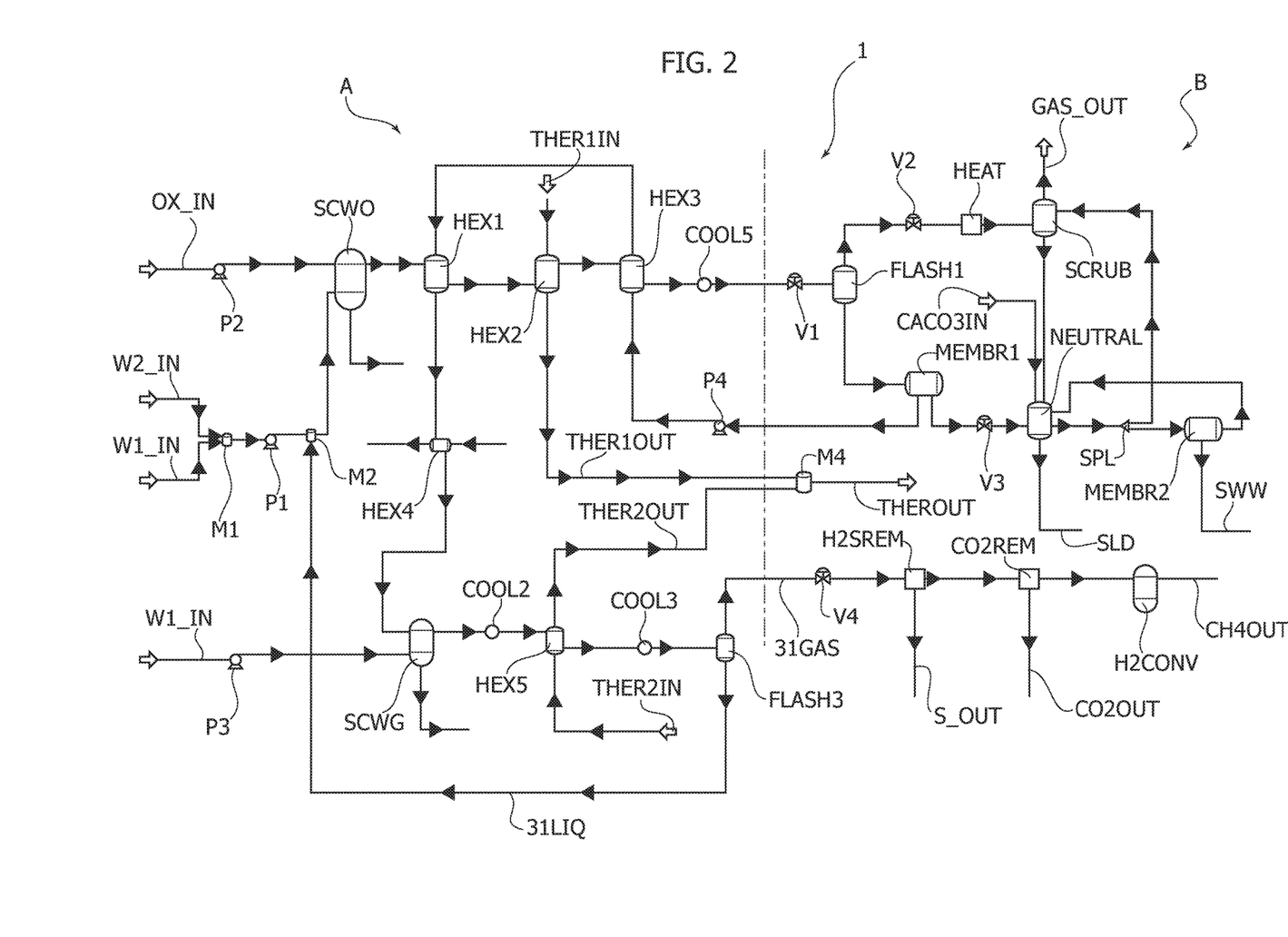
FIG. 2 is a schematic overall view of a preferred embodiment of a waste-disposal plant according to the present invention.

In greater detail, the feeding system is configured for feeding to the plant 1 at least two organic currents of waste W1_IN, W2_IN and Wn_IN, the latter being assumed as the n-th current, possibly optional: as mentioned, the organic currents are at least two; in the specific example of FIG. 2 the references W1_IN, W2_IN, W3_IN will be used.

Examples of organic waste constituting one or more of the above currents include:
  a solid organic current such as waste char from plants for pyrolysis or thermal cracking of waste and/or biomasses such as paper, cardboard, plastics, tyres, rubbers, fibres, resins, fabrics, WDF (Waste-Derived Fuel), biomasses such as those deriving from pruning, wood, etc.;

a solid organic current such as petroleum coke, carbon black, pharmaceuticals, pesticides, dioxins;

an organic current in liquid phase comprising, for example, mixtures of organic compounds such as heavy waste oils from pyrolysis plants or plants for thermal cracking of waste and/or biomasses such as paper, cardboard, plastics tyres, rubbers, fibres, resins, fabrics, WDF (Waste-Derived Fuel), biomasses such as those deriving from pruning, wood, etc., a liquid organic current such as oils, solvents, paints, etc.

As regards the at least two organic currents of waste, the feeding system is configured for feeding these currents in parallel to the reactors SCWO and SCWG, meaning thereby a selective feed to one reactor (SCWO) or the other reactor (SCWG) according to the characteristics of the waste carried by the various organic currents: this is represented in the diagram of FIG. 1, in particular by the double-headed arrow that spans the perimeter of the plant 1 itself.

Of course, it is also possible for one or more of the currents of waste entering the plant to be constituted by inorganic waste or in any case waste with a non-preponderant organic charge such as, by way of non-exhaustive example, the aqueous currents of residential, commercial, and/or industrial wastewaters, washing waters, contaminated and/or polluted waters (see, for example a current WW_IN, as will be described hereinafter), residential, commercial, and industrial sludges or sludges coming from quarrying or refining mining activities, etc., provided that at least two organic currents are present.

In the present description, the terms "organic" and "inorganic" are used with reference to the most common definition whereby an organic compound is defined as a compound in which one or more carbon atoms are bound via covalent bond to atoms of other elements with the exclusion of carbon monoxide, carbon dioxide, and carbonates.

The waste-feeding system is moreover configured for feeding and/or circulation of one or more aqueous currents including:

at least one aqueous current PLS, which is obtained by cooling of the effluent (reaction products) of the reactor SCWG and contains non-gasified organic and/or inorganic waste: this current, as will be seen, is circulated from the reactor SCWG to the reactor SCWO to obtain a complete mineralization and inertization of the waste contained therein;

at least one aqueous current WW_IN, possibly containing organic and/or inorganic species, in amounts such as to reach the necessary titre or water consumption in the two reactors; these one or more aqueous currents WW_IN may be constituted, for example, by currents of waste coming from residential, commercial, and/or industrial wastewaters, washing waters, waters contaminated and/or polluted by organic and inorganic chemical agents (for example, waters of paper factories, bilge waters, waters from tanning and leather industries, emulsions of industrial waters, percolates of urban-waste dumps, waters to be purified on account of the presence of surfactants, hydrocarbons, herbicides, pesticides, heavy metals, etc.); and possibly, a current of substantially pure water PW, which comes from the reactor SCWO and is fed to the supercritical-water gasification reactor SCWG as water for the gasification reaction (it may be supplied, as will be seen, already in supercritical conditions in order to provide thermal integration within the plant 1), in the case where the aqueous current WW_IN fed to the supercritical-water gasification reactor SCWG has a flow rate that is insufficient to meet the demand of the supercritical-water gasification reactor, so as to restore a required flow rate value; in particular, the supply of the current PW takes place in the case where the flow rate of the current WW_IN is not sufficient to reach the necessary titre for sustaining the reactions in the reactors SCWO and SCWG, or else in the case where the current WW_IN has characteristics of soiling such as to inhibit use thereof in heat exchangers necessary for thermal integration between the two reactors SCWO and SCWG (this because currents of extremely polluted waste waters can lead to occlusions and malfunctioning in general of the heat exchangers); it should be noted that the exploitation of the current PW reduces further the environmental impact of the plant 1 in so far as it eliminates the need to resort to spring water (where available) for integration of the amount of water of the current WW_IN, which—instead—would in any case render the process less sustainable from the environmental standpoint on account of exploitation of primary resources (spring water).

It should be noted that the currents PLS and PW are currents that circulate within the plant 1 and flow in series through the two reactors SCWO and SCWG, whereas the current (or currents) WW_IN are supplied from outside the plant 1. It should moreover be noted that there may exist further passages and/or exchanges of waste between the two sections of the plant (SCWG and SCWO) according to needs linked to destruction of the waste itself.

The products leaving the plant 1 in general include inert ashes IA, water suitable for being discharged into the environment SWW, and gas that is innocuous SFG as regards the oxidation section (the reactor SCWO and the unit for after-treatment of the products of reaction thereof), whereas it includes purified synthesis gas SG as regards the gasification section (the reactor SCWG and the unit for after-treatment of the products of reaction thereof).

Globally, the plant yields to the outside environment also useful energy UE. Furthermore, within the plant there is transfer of energy E between the oxidation and gasification sections, thanks to the thermal integration (and energy integration in general) between the two sections. In particular, as will be seen, part of the thermal energy produced in the oxidation reactor SCWO is exploited to heat the water entering the gasification reactor SCWG, in any case recovering the other part in the form of process heat, and earmarking it, through the thermovector fluid, for various uses. In other words, present in the plant 1 is also a system for circulation of thermal energy between the supercritical-water oxidation section and the supercritical-water gasification section configured for enabling exploitation of part of the heat produced by the supercritical-water oxidation reaction in order to meet the energy requirements of the gasification reaction.

With reference to FIG. 2, a plant 1 according to a preferred embodiment of the invention will now be described in detail, with reference to the plant layout presented therein.

Figure 2A:
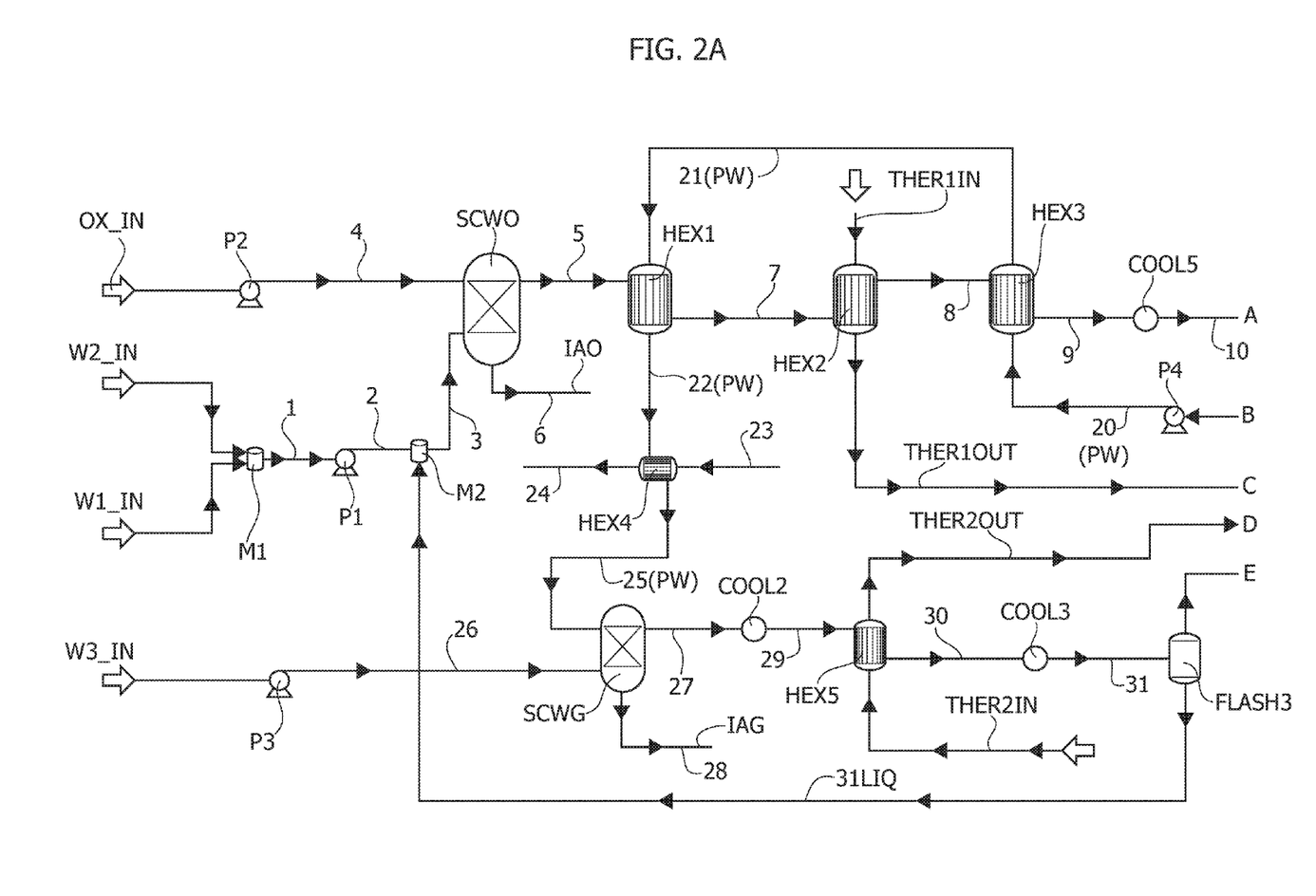
FIGS. 2A and 2B are enlarged views of two sections of the plant corresponding, respectively, to the sections designated by the letters A and B in FIG. 2 for greater clarity of representation.
Figure 2B:
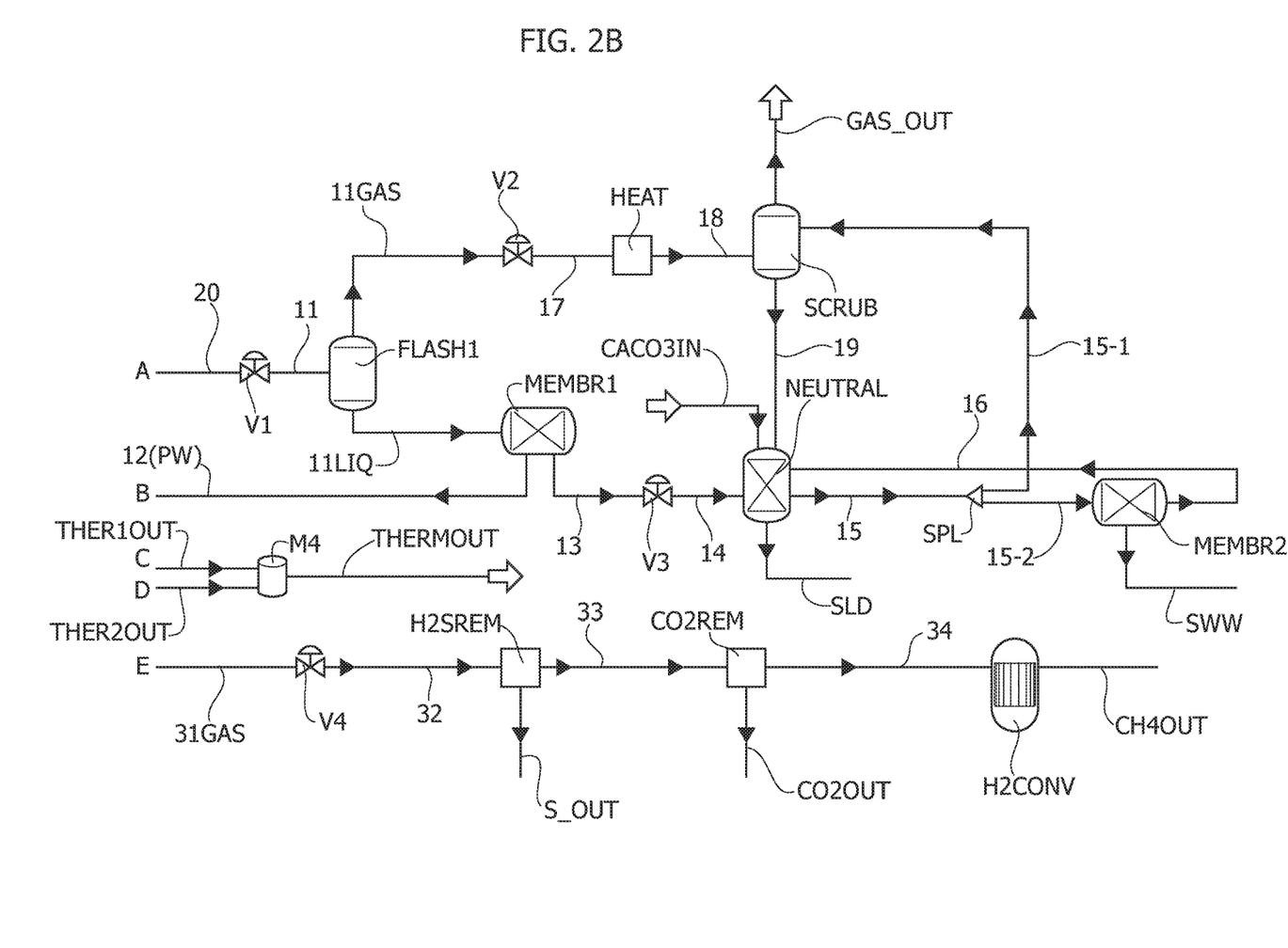

The description will be developed mainly with reference to FIGS. 2A and 2B, which illustrate two sections of the plant of FIG. 2 at an enlarged scale, and both of which bear five terminations A, B, C, D, E in the points of division of the scheme, to indicate the continuity of the two representations.

With reference to FIGS. 2A and 2B, the plant includes seven input mass flows and nine output mass flows. The input mass flows include:

i) an input flow of oxygen OX_IN for supply of the reactor SCWO, ii-iii) the organic currents of waste W1_IN, W3_IN, which constitute the organic currents of waste and correspond, respectively and by way of example, to carbon black and heavy oil with medium sulphur content; by the term "carbon black" is meant in general (merely by way of non-exhaustive example) carbon black itself, soot, coal, coke, pet-coke, and char from plants for pyrolysis and/or thermal cracking of waste and biomasses; the term "heavy oil with medium sulphur content" is, instead, intended to comprise, merely by way of non-exhaustive example, waste oils from plants for pyrolysis and/or thermal cracking of waste and biomasses, and more in general oils, solvents, and paints; in this connection, there may be envisaged—possibly as integral part of the feeding system of the plant 1—a plant for pyrolysis or cracking of waste and/or biomasses of various nature and or other units for physico-chemical pre-treatment of the incoming waste in its crude condition (for example, tyres, rubbers, resins, plastics, fibres, paper, cardboard, WDF, etc.); this may become necessary in the case where the waste to be treated does not possess in its raw form—i.e., in the form in which it reaches the plant 1—characteristics suitable for treatment in the plant 1 itself;

iv) the current W2_IN, which functionally corresponds to the aqueous current WW_IN, possibly containing organic and/or inorganic species, and constituted, for example, by percolate from rubbish dumps (water contaminated by organic chemical agents that determine its chemical oxygen demand—COD—and biological oxygen demand—BOD—and by inorganic chemical agents such as heavy metals, ammonia, etc.; in the specific example considered herein, as will emerge more clearly from the ensuing description, the flow rate of the current W2_IN is not suitable or not sufficient to reach the necessary titre (or water consumption) in the two reactors SCWO and SCWG;

v-vi) a first flow and a second flow of thermovector fluid THER1IN and THER2IN, for example diathermic oil, but also, for example, water vapour, molten salts, and any other thermovector fluid available;

vii) an input flow of calcium carbonate CACO3IN, or in general a flow of any Lewis base capable of neutralizing acid currents with formation of saline precipitates.

As regards the output mass flows, the plant includes the following:

i) an output flow of gas GAS_OUT basically containing carbon dioxide, water vapour, and small amounts of oxygen and nitrogen;

ii) a flow of inert solid waste SLD basically consisting in calcium sulphites and sulphates obtained by neutralization with calcium carbonate of an aqueous solution of sulphurous acid and sulphuric acid, respectively;

iii) an output flow of purified water SWW;

iv) a flow of inert ashes at output from the reactor SCWO, designated by the reference IAO;

v) a flow of inert ashes at output from the reactor SCWG, designated by the reference TAG;

vi) an output flow of biomethane CH4OUT, which constitutes a product of the plant 1 that can be used elsewhere, for example in a residential, commercial, or industrial gas-distribution grid;

vii) an output flow of elementary sulphur S_OUT;

viii) an output flow of carbon dioxide CO2OUT;

ix) an output flow of thermo-vector fluid THEROUT, which is equal to the sum of the flows THER1OUT and THER2OUT, which are in turn equal to the flows THER1IN and THER2IN.

The components of the plant 1 and the modalities of connection between them will be now be described. For simplicity of description, the connections between the components—which are all such as to set up a fluid communication—will be referred to as a whole as "connection", in so far as it is generally known in the art how such connections have to be made.

The plant 1 includes a first mixing unit M1, which receives at input the flows W1_IN and W2_IN. The unit M1 is in fluid communication, by means of a connection 1, with the intake port of a first pump P1, the delivery port of which is in fluid communication, by means of a connection 2, with a second mixing unit M2.

The second unit M2 is in fluid communication, by means of a connection, 3 with the supercritical-water oxidation reactor SCWO. The latter is moreover in fluid communication with a second pump P2, which sends to the reactor SCWO the input flow of (cryogenic) oxygen OX_IN, through a connection 4.

In alternative embodiments, there may be used, instead of the input flow of cryogenic oxygen OX_IN, a flow of compressed air at the operating pressure of the reactor SCWO, which contains—in addition to the oxygen necessary for operation of the reactor SCWO at a flow rate equal to the flow rate OX_IN—also nitrogen, carbon dioxide, and traces of noble gases. In this variant, an air compressor will have to be provided in the plant of FIG. 2 for feeding said flow to the reactor SCWO.

The reactor SCWO further includes two outlet ports, the first being in view of a discharge exiting from which is the flow IAO (here represented schematically as connection 6, in actual fact a collection environment on the bottom of the reactor), and the second being in fluid communication with a first heat exchanger HEX1—in particular with a first flow path therein—by means of a connection 5, which is configured for carrying the flow of reaction products of the reactor SCWO.

The above flow of reaction products of the reactor SCWO traverses the heat exchanger HEX1, coming out through a connection 7, by means of which the heat exchanger HEX1 is in fluid communication with a second heat exchanger HEX2, in particular with a first flow path therein. It should be noted that the second flow path of the heat exchanger HEX2 carries the flow THER1IN, which exits from the heat exchanger HEX2 as flow THER1OUT.

Starting from the heat exchanger HEX2 is a connection 8, by means of which the first flow path of the heat exchanger HEX2 is in fluid communication with a third heat exchanger HEX3—in particular with a flow path therein—and where the connection 8 is once again configured for carrying the reaction products of the reactor SCWO.

The path of the reaction products of the reactor SCWO out of the heat exchanger HEX3 proceeds through a connection 9, which sets up a fluid communication with a cooler COOLS. The latter is in fluid communication with a lamination valve V1 by means of a connection 10, whereas a connection 11 downstream of the valve V1 sets up a fluid communication with a first liquid/gas separator FLASH1.

The separator FLASH1 includes two outlet ports, each configured for draining of a corresponding (liquid or gaseous) phase of the reaction products of the reactor SCWO. In particular, starting from a first outlet port of the separator FLASH1 is a connection 11LIQ configured for draining the reaction products in the liquid phase, whereas starting from a second outlet port is a connection 11GAS configured for draining the reaction products in the gaseous phase.

The connection 11LIQ gives out into an inlet port within a first membrane separator MEMBR1, which is provided with two outlet ports.

Starting from a first outlet port is a connection 12, which sets up a fluid communication with the intake port of a pump P4, whereas starting from a second outlet port is a connection 13, which reaches a lamination valve V3. The connection 11GAS is instead in direct view of a lamination valve V2, which enables reduction of the pressure of the fluid that traverses it (in this case gas). Starting downstream of the valve V3 is a connection 14, which gives out into the inlet port of a neutralizer NEUTRAL.

The neutralizer NEUTRAL receives at input the flow of calcium carbonate CACO3IN (or, as has been said, any other Lewis base capable of neutralizing acid currents with formation of saline precipitates), and includes two outlet ports. A first outlet port is in fluid communication with a splitter SPL by means of a connection 15, whereas exiting from the second outlet port is the inert waste SLD (hydrated calcium sulphate—gypsum).

Also the splitter SPL includes two outlet ports, where a first outlet port is in fluid communication with the inlet port of a sulphur scrubber SCRUB by means of a connection 15_1, whereas a second outlet port is in fluid communication with the inlet port of a second membrane separator MEMBR2. The separator MEMBR2 is also provided with two outlet ports, where at output from a first outlet port is the flow rate SWW, whereas a second outlet port is in fluid communication with a second inlet port of the neutralizer NEUTRAL by means of a recirculation connection 16.

Set downstream of the valve V2 is a connection 17, which goes from the connection 11GAS to a heat exchanger HEAT, from which fluid communication proceeds with a connection 18 to a second inlet port of the sulphur scrubber SCRUB. The scrubber SCRUB also includes two outlet ports, in particular a first outlet port exiting from which is the flow rate GAS_OUT of purified discharge gas, and a second outlet port, which is in fluid communication with a third inlet port of the neutralizer NEUTRAL.

The delivery port of the pump P4 (which processes the flow passing in the connection 12) is in fluid communication, by means of a connection 20, with a second flow path within the heat exchanger HEX3 (where heat exchange is obtained with the fluid that flows in the respective first path). The flow that passes along the second flow path of the heat exchanger HEX3 exits therefrom through a connection 21, by means of which a fluid communication is set up with a second flow path in the heat exchanger HEX1 (where heat exchange is obtained with the fluid that flows in the respective first path). The flow passes along the second flow path of the heat exchanger HEX1 exits therefrom through a connection 22, by means of which a fluid communication is set up with a fourth heat exchanger HEX4, in particular with a first flow path therein. Flowing in the second flow path of the heat exchanger HEX4 (inlet connection 23 and outlet connection 24) is, instead, a diathermic thermovector fluid, which is extraneous to the plant, for example (once again) diathermic oil.

The flow that passes through the heat exchanger HEX4 exits therefrom through a connection 25, by means of which a fluid communication is set up with an inlet port of the reactor SCWG.

It should in any way be noted that the heat exchanger HEX4 is generally optional, given that it has the sole function of modulating the inlet temperature of the gasification reactor: in alternative embodiments, the plant 1 may be without it, with consequent direct connection between the outlet of the second flow path of the heat exchanger HEX1 and the (first) inlet port of the reactor SCWG (which is a port for feeding water for the gasification reaction, as will be seen).

The reactor SCWG is moreover fed with the organic current of waste W3_IN (in this embodiment) by means of a pump P3. The delivery of the pump P3 for this purpose is in fluid communication, by means of a connection 26, to a second inlet port of the reactor SCWG. The latter further includes two outlet ports, in particular a first outlet port starting from which is a connection 27, configured for carrying the reaction products of the reactor SCWG and setting up a fluid communication with the inlet port of a cooler COOL2, and a second outlet port corresponding to the discharge for the inert ashes IAG (here represented schematically as a connection 28, in actual fact a collection environment on the bottom of the reactor).

The cooler COOL2 further includes an outlet port, which is in fluid communication, by means of a connection 29, with a fifth heat exchanger HEX5, in particular with a first flow path therein. It should be noted that the second flow path of the heat exchanger HEX5—as likewise of the heat exchanger HEX2—carries the flow THER2IN, which exits from the heat exchanger HEX5 as flow THER2OUT and is aggregated by means of a mixing unit M4 to the flow THER1OUT resulting in the discharge of thermovector fluid THERMOUT.

The first flow path of the heat exchanger HEX5 proceeds out of the plant by means of a connection 30, which sets up a fluid communication with the inlet port of a cooler COOL3. Starting from the outlet port of the cooler COOL3 is a connection 31, which gives out into the inlet port of a third liquid/gas separator FLASH3. The separator FLASH 3 includes two outlet ports, the first, configured for carrying the reaction products of the reactor SCWG in the gaseous phase, being in fluid communication with a lamination valve V4 by means of a connection 31GAS, and the second being in fluid communication with a second inlet port of the mixing unit M2 by means of a connection 31LIQ, which is configured for carrying the reaction products of the reactor SCWG in the liquid phase.

Starting downstream of the valve V4 is a connection 32, which sets up a fluid communication with the inlet of a unit for adsorption of hydrogen sulphide H2SREM, which is configured for processing the flow of gas coming from the connection 31GAS, purging it of the excess hydrogen sulphide. The hydrogen sulphide is thus converted into elementary sulphur and expelled through a discharge S_OUT.

The outlet of the unit H2SREM is in fluid communication with the inlet of a carbon-dioxide trap CO2REM by means of a connection 33. The trap CO2REM is configured for processing the flow of gas that comes from the connection 31GAS (and has already passed through the unit H2SREM) purging it of the excess carbon dioxide, which is hence released into the atmosphere through the discharge CO2OUT.

Finally, the outlet of the trap CO2REM is in fluid communication with an isothermal catalytic converter H2CONV, within which the flow of gas that leaves the trap CO2REM through the connection 34 is made to react, giving rise to the flow of biomethane CH4OUT.

Operation of the plant 1 is described in what follows.

As a preliminary note on operation of the reactors SCWO and SCWG, in a way per se known, in the supercritical-water oxidation reactor SCWO a treatment of supercritical-water oxidation of organic waste is carried out at temperatures higher than the critical temperature of water (T=374°

C.) and at a pressure above the critical pressure of water (p>22 MPa). The organic matter is completely oxidised to carbon dioxide by the cryogenic oxygen (supplied through the pump P2—flow OX_IN, alternatively oxygen present in air fed by means of a compressor, as has already been said) within the aqueous medium. In this process the toxic and highly dangerous waste can be converted into compounds that can be released safely into the environment.

Complete miscibility of the organic compounds with supercritical water avoids the limitations on the mass transfer and on the degree of reaction of the chemical species that afflict incinerators of a known type, in which emissions of undesired chemical species in any case take place.

Instead, in the reactor SCWO the organic compounds are completely oxidised to carbon dioxide and water. The hetero-atoms, such as, for example, chlorine, sulphur, or phosphorus, if present in the organic current of waste, are converted into mineral acids (hydrochloric acid HCl, sulphuric acid $H_2SO_4$, or phosphoric acid $H_3PO_4$), whereas the nitrogen possibly contained in the flow of waste principally forms inert nitrogen $N_2$ and a small amount of nitrogen dioxide $N_2O$.

The dioxins and nitrogen oxides $NO_X$ generally do not form on account of the low process temperatures. In the case where they are present at input, the dioxins would be completely oxidised to carbon dioxide, water, and mineral acids. The salts that derive from neutralization of the acids can be precipitated by the supercritical mixture and extracted from the bottom of the reactor SCWO together with other inorganic ashes.

Provided in what follows are some examples of global reactions of oxidation of waste that take place in the reactor SCWG:

$C+O_2 \rightarrow CO_2$                                       Carbon:

$C_xH_yO_z+(x+y/4-z/2)O_2 \rightarrow xCO_2+y/2H_2O$    Organic compound:

$C_6H_{10}O_5+6O_2 \rightarrow 6CO_2+5H_2O$                  Cellulose:

$Cl_2-C_6H_2-O_2-C_6H_2-Cl_2+11O_2 \rightarrow 12CO_2+4HCl$ Dioxin(PCCD):

The process time for complete conversion of the organic waste into oxidised and non-dangerous chemical species is of the order of magnitude of seconds or minutes, depending upon the type of organic waste and its water concentration. On account of the low values of the dielectric constant and of the ionic product of water, the ionic reactions are inhibited. As a result, it is the radicals that promote the reaction mechanism.

The global oxidation reactions in the reactor SCWO have the following differential expression:

$d[S]/dt = -k[S]^a[O_2]^b$ where S is the compound to be oxidised. The constant k follows a functional dependence upon the temperature T according to Arrhenius law, and hence may be expressed as $k=A \cdot \exp(-E_a/RT)$, where $E_a$ represents the activation energy of the reaction.

As regards, instead, the reactor SCWG, a current of water and a current of organic waste that are energetically suitable for treatment in the reactor are supplied thereto in supercritical conditions. The supercritical water has the role of reaction medium for the gasification that leads to hydrolysis reactions in parallel with pyrolysis reactions.

Supercritical-water gasification is a direct way of formation of gases such as hydrogen ($H_2$), carbon monoxide (CO), carbon dioxide ($CO_2$), methane ($CH_4$), and light hydrocarbons ($C_2$-$C_3$), without formation of carbon residue.

After separation of the gases from the water, a synthesis gas is obtained that is at high pressure and is useful for subsequent applications.

The kinetic scheme of the reaction is very complex: it comprises various steps with formation of a wide range of reaction intermediates through a mechanism promoted by radicals. By way of orientation, a mechanism of reaction may be assumed as reference, which comprises a reaction of reforming of hydrocarbons of the type:

$C_xH_y+xH_2O \rightarrow (x+y/2)H_2+xCO$ and a water-gas transition phase, which enables conversion of carbon monoxide into hydrogen:

$CO+H_2O \rightarrow H_2+CO_2$ and finally a methanation phase, which enables conversion of hydrogen into methane:

$CO+3H_2 \rightarrow CH_4+H_2O$

Since the methanation reaction is markedly exothermic, it is not favoured at temperatures of 600° C. or higher, such as the ones generally reached in SCWG reactors. For this reason, the methane concentration is low when gasification takes place at high temperatures (T>500° C.). In operation at high temperature, the main product is made up of hydrogen ($H_2$), carbon dioxide ($CO_2$), carbon monoxide (CO), and methane ($CH_4$). The sulphur present in the current of organic waste is reduced to hydrogen sulphide ($H_2S$). The insoluble salts that may be present in the reactor are then recovered from the bottom of the reactor as precipitated salts.

This having been said, in the embodiment of the plant 1 represented in FIGS. 2, 2A, and 2B, the organic current of waste W1_IN corresponds to a flow rate of 2000 kg/h of percolate from rubbish dumps (the value is to be considered purely as an example for this plant), the organic current of waste W2_IN corresponds to a flow rate of 320 kg/h of carbon black, whereas the organic current of waste W3_IN corresponds to a flow rate of 500 kg/h (the value is to be considered purely as an example for this plant) of heavy oil from pyrolysis (with medium sulphur content).

The flow OX_IN corresponds to a flow of liquid oxygen of 920 kg/h (the value is to be considered purely as an example for this plant) that comes from a storage tank at a temperature of −153° C. and at a pressure of 10 bar. Alternatively, it is possible use a flow of compressed air that is equivalent to the above flow of cryogenic oxygen OX_IN. As may be noted from FIG. 2A, upstream of the plant 1 the waste-feeding system is configured for feeding selectively the organic currents to the reactor SCWO or to the reactor SCWG, which are hence supplied in parallel with the organic currents and in a selective way on the basis of criteria of optimisation of efficiency and effectiveness of the treatment, as well as to prevent occlusions and scaling in the reactors according to the chemico-physical characteristics of the currents themselves. It should moreover be borne in mind that the waste-feeding system referred to in the present description is not limited just to the machines (namely, the pumps P1, P3) that feed the waste to the plant 1, but also comprises all the remaining pumps or plant components, including the connections between components, which make it possible to set up the conditions for circulation of the (organic and inorganic) currents. Given these premises, forming hence part of the waste-feeding system are also the separators FLASH1, FLASH3, MEMBR1, MEMBR2 and even the reactors SCWO and SCWG themselves, which create the conditions of pressure (and temperature) of the currents of fluid necessary for their circulation.

In this specific case, the heavy oil that constitutes the current W3_IN is particularly suitable for direct treatment in the reactor SCWG as compared to the current W1_IN. The reason for this is the low content of species that are to generate ashes in the process of conversion and the high gasifiability as compared to the current W1_IN, which enables more contained reaction times and a higher degree of conversion of the reagents, with consequent lower formation of bituminous products that would cause scaling and would occlude the lines downstream of the reactor SCWG (this being, instead, likely in the case of direct gasification of the current W1_IN). For this reason, the current W3_IN is directly sent on via the pump P3 into the connection 26 at inlet to the reactor SCWG.

The percolate from rubbish dumps and the carbon black (currents W1_IN and W2_IN) are, instead, mixed inside the mixing unit M1, and the resulting mixture is sent on, through the connection 1, to the intake of the pump P1. From the delivery of the pump P1 the mixture enters the mixing unit M2, where it is further enriched with a liquid current with aqueous base (which will be described hereinafter) that flows in the connection 31LIQ.

The mixing unit M2 then sends on the mixture as a whole (percolate from rubbish dumps, carbon black, and aqueous current within the connection 31LIQ) to the inlet of the reactor SCWO through the connection 3 for the supercritical-water oxidation treatment.

The supercritical-water oxidation reaction proceeds according to the modalities described previously, and the reaction products exit in part through the connection 5 as mixture of products in supercritical aqueous phase and in part as inert solid products, or inert ashes IAO, comprising the possible precipitated salts produced during the supercritical-water oxidation reaction.

The products of the reaction of oxidation are then carried into the connection 5 within the first flow path of the heat exchanger HEX1 (where they yield heat to the fluid that flows in the second flow path and that comes from the connection 21, as will be described), and exit therefrom through the connection 7.

From here the reaction products traverse the first flow path of the heat exchanger HEX2, where a further transfer of heat occurs, this time to the thermovector fluid (flows THER1IN, THER1OUT) that flows in the second flow path of the heat exchanger HEX2.

The flow of the reaction products of the reactor SCWO then exits from the heat exchanger HEX2 through the connection 8, and from here flows into the heat exchanger HEX3, within which there occurs a further heat exchange with transfer of heat to the fluid that flows within the second flow path of the heat exchanger HEX3 and that comes from the duct 20 (as will be described in hereinafter).

The flow of reaction products—at a temperature appreciably lower than at the outlet of the reactor SCWO—leaves the heat exchanger HEX3 and is sent on, through the connection 9, to the cooler COOLS. Then it enters the separator FLASH1 after traversing the lamination valve V1, in which a first reduction of pressure is obtained to values compatible with the mechanical resistance of the membranes of the unit MEMBR1. The flow of reaction products, which, as has been said, is in the form of aqueous solution, is then separated into the liquid and gaseous phases by the separator FLASH1.

The gaseous component of the flow of reaction products leaves the separator FLASH1 through the connection 11GAS and mainly contains carbon dioxide $CO_2$, sulphur dioxide ($SO_2$), and water vapour ($H_2O$). From here the gaseous mixture is brought to atmospheric pressure by means of the valve V2, is heated in the heat exchanger HEAT by one of the currents to be cooled (e.g., the current that flows in the connections 9, 27, or 31) and enters the sulphur scrubber SCRUB through the connection 18. Preferably, the sulphur scrubber operates via chemical absorption of SOx in water added with calcium carbonate. The scrubbing operation leads to release into the atmosphere of a discharge gas GAS_OUT made up of carbon dioxide, water vapour, a small amount of oxygen and nitrogen, and possibly traces of sulphur dioxide or trioxide below the limits of law.

The component in liquid phase of the flow of reaction products—which basically consists of acid water containing a certain amount of sulphur dioxide ($SO_2$) produced in the supercritical-water oxidation reaction together with sulphur trioxide ($SO_3$) in the form of sulphuric acid $H_2SO_4$—leaves the separator FLASH1 through the connection 11LIQ and enters the membrane separator MEMBR1, where it is separated into a flow of substantially pure water, which is sent on into the connection 12 to the intake of the pump P4. This flow of substantially pure water is constituted by water that is practically free from salts and other species, the purity of which, which is normally quite high, depends upon the performance of the membranes used. It is a water more than adequate for its use for subsequent superheating and supply at input to the gasification reactor, as will be described hereinafter.

The pump P4 sends the flow of pure water (current PW) into the connection 20 and through the heat exchanger HEX3, where the water undergoes a first heating on account of the heat exchange with the flow of reaction products that flow in the first flow path of the heat exchanger HEX3. Then the heated water exits from the heat exchanger HEX3 through the connection 21 and enters the second flow path of the heat exchanger HEX1, where it is heated up to supercritical conditions on account of the strong flow of heat exchanged with the reaction products at high temperature that exit from the reactor SCWO.

The supercritical water then leaves the heat exchanger HEX1 and proceeds towards the inlet of the reactor SCWG through the connection 22, the heat exchanger HEX4 (generally not used, but provided for the purposes of a greater operating flexibility as regards modulation of the gasification temperature at values lower than 600° C., with consequent increase in methane yield), and the connection 25.

As will be appreciated, this means that part of the aqueous current that has already traversed the reactor SCWO is preheated in the heat exchangers HEX1 and HEX3 by the reaction products of the reactor SCWO itself before it enters the reactor SCWG. It will thus be clearly understood how the aqueous current PW, flowing in series through the reactors SCWO and SCWG, provides thermal integration (in general energy integration) between the oxidation section and the gasification section within the plant 1.

The other flow that exits from the membrane separator MEMBR1 is substantially acid water that traverses the connection 13, the lamination valve V3, and the connection 14 and enters the neutralizer NEUTRAL. Within the neutralizer the acid aqueous solution is neutralized thanks to the contribution of the input flow of calcium carbonate CACO3IN, producing a solid SLD as waste (mixture of calcium sulphate and sulphite). It should moreover be noted that, from the neutralizer NEUTRAL, a current of turbid water containing $CaCO_3$ is fed, through the connection 15-1, to the sulphur scrubber SCRUB, which then removes from the gaseous current GAS_OUT the sulphur oxides SOx exceeding the limits of law, and then returns to the neutralizer NEUTRAL itself, through the connection 19.

The flow that leaves the neutralizer NEUTRAL reaches, through the connection 15, the splitter SPL, which sends a first part of flow of fluid containing excess calcium carbonate into the connection 15-1 so that it enters the sulphur scrubber SCRUB to eliminate the residual gaseous sulphur dioxide.

The remaining part of flow is sent on to the connection 15-2 and enters the membrane separator MEMBR2, which discharges pure water SWW into the environment for subsequent uses and recirculates the residual flow, which still contains acid and/or sulphurated species, towards the neutralizer NEUTRAL for a further neutralization/precipitation treatment.

To return to the supercritical-water gasification reactor SCWG, it is supplied with the heavy oil (current W3_IN) by the pump P3 through the duct 26, and is fed by supercritical water preheated by the heat exchangers HEX1 and HEX3 as described previously.

The heavy oil is treated in the reactor SCWG according to the modalities described previously, resulting in the emission of inert ashes IAG (discharge 28) and a flow of reaction products that leaves the reactor through the connection 27. From here, the flow of reaction products enters the cooler COOL2, by which it is cooled before entering the first flow path of the heat exchanger HEX5. Inside this, the flow of the reaction products is cooled by a flow of thermovector fluid THER2IN that flows in the second flow path, and exits at a lower temperature into the connection 30. It should be noted that the flows THER1OUT and THER2OUT, which are both characterized by a higher temperature than the corresponding input flows THER1IN and THER2IN, are mixed in the mixing unit M4, and sent out of the plant as flow THERMOUT for subsequent uses, for example for the production of electrical energy by means of thermodynamic cycles based upon organic fluids (ORC—Organic Rankine Cycle).

The flow of reaction products of the reactor SCWG then leaves the heat exchanger HEX5 through the duct 30 and proceeds towards the cooler COOL3, and then—at a lower temperature—proceeds into the connection 31 of the liquid/gas separator FLASH3.

The separator FLASH3 separates the liquid and gaseous phases of the reaction products of the reactor SCWG: the fraction in the liquid phase (which contains the non-gasified organic species in the reactor SCWG) is recirculated towards the mixing unit M2 through the connection 31LIQ and is then sent on to the reactor SCWO for treatment after prior mixing with the currents W1_IN and W2_IN within the mixing unit M2. In general, it should be noted that, in other embodiments, only one of the organic currents fed to the plant 1 can reach the mixer, in addition to the current that flows in the connection 31LIQ.

It should be noted, among other things, that all the aqueous flows within the plant 1 are supplied continuously by the process of disposal and recovery of the waste itself, preventing consumption of precious water from the environment, with evident advantages in terms of environmental impact and ecologic sustainability of the process.

The gaseous-phase fraction of the reaction products of the reactor SCWG is, instead, sent on into the connection 31GAS, traverses the lamination valve V4 and the connection 32, and enters the hydrogen-sulphide trap H2SREM. The flow rate of elementary sulphur S_OUT is released by the latter into the environment, whereas the depurated gaseous flow that leaves the trap H2SREM traverses the connection 33 and enters the carbon-dioxide trap CO2REM, from which the flow of carbon dioxide CO2OUT is released into the environment (or else sent on for other uses).

Finally, the gaseous flow further depurated is sent on into the connection 34 and then into the isothermal catalytic converter H2CONV, used for converting the residual hydrogen, carbon monoxide, and carbon dioxide into methane and water, in order to meet the specifications of law for entry into the biomethane grid (in particular, the standard 498/2014 of the Authority for Electricity and Gas and the standard UNI/TR 11537), and exits as flow CH4OUT. It should hence be noted that the ensemble of the traps H2SREM, CO2REM and of the isothermal catalytic converter H2CONV in effect provides an assembly for after-treatment of the gaseous fraction of the reaction products of the reactor SCWG.

It should here be emphasised that the entire block of devices for treating the gases and liquids described above becomes necessary because the organic currents fed in this example contain significant amounts of sulphur, which forms $SO_2$ and $SO_3$ in the oxidation reaction and $H_2S$ in the gasification reaction. In the case where the organic currents at input were not to contain sulphur, the method would remain substantially unaltered as regards connection and thermal integration of the two reactors SCWO and SCWG, whereas the treatments of sulphur scrubbing of the liquid and gaseous currents would not be necessary.

As a further note, it has been said previously that the heat exchanger HEX4 is not strictly necessary for operation of the plant 1. An example of operating condition in which it may prove useful is the one in which the reactor SCWG is required to operate at a lower temperature in the presence of a gasification catalyst. The heat exchanger HEX4 would hence act as cooler.

From what has been described previously, operation at a lower temperature enables a higher methane production to be obtained since it favours the methanation reaction. In this connection, the heat exchanger HEX4 can be traversed by a diathermic thermovector fluid like the heat exchangers HEX2 and HEX5 so as to cool the water that is itself already in supercritical conditions after it has passed through the heat exchangers HEX3 and HEX1 for feeding the reactor SCWG at the required temperature.

On the basis of the above description, the advantages listed below of the plant 1 and of the method for disposal of waste according to the invention may hence be appreciated.

i) Part (or all, in the case of supply with currents poor in organic components) of the thermal energy generated by the combustion of waste in the reactor SCWO is used to assist the reactor SCWG, which requires thermal energy for heating the water and currents of waste up to the operating temperature necessary for the gasification reaction to take place, in so far as this temperature is lower than that of the reactor SCWO.

ii) Two different flows at high pressure are obtained from the supercritical-water gasification reaction after cooling of the reaction products of the reactor SCWG. In particular, there are obtained a flow in the gaseous phase that contains precious gases such as hydrogen and methane, and a flow in the liquid phase that contains the majority of the water fed to the reactor SCWG, all the organic species that have not reacted or have only partially reacted, as well as noxious species such as hydrogen sulphide $H_2S$ and possible other inorganic species dissolved in water. This residue, especially hydrogen sulphide, would give rise to serious problems of disposal in a plant comprising a single supercritical-water gasification reactor.

Instead, in the present combined plant they are simply fed to the supercritical-water oxidation section where they are completely destroyed. Supercritical-water oxidation is in fact a so-called BAT (Best Available Technology), known for being capable of treating virtually any pollutant with the result of producing a flow of products at output that are perfectly safe. Furthermore, the provision of an after-treatment unit that is able to depurate the flow of products leaving the reactor SCWG from noxious species such as hydrogen sulphide $H_2S$ (thanks to the trap H2SREM), converting it into elementary sulphur, certainly constitutes a highly qualifying element for the plant 1.

iii) Part of the thermal energy produced in the oxidation reactor SCWO is exploited in order to heat the water at input to the gasification reactor SCWG in any case recovering in the form of process heat the other part, and earmarking it, through the thermovector fluid, for various uses. These uses may comprise the production of electrical energy in an ORC (Organic Rankine Cycle) assembly, production of steam for industrial uses, district heating, supply of high-quality thermal energy to other process units and/or other equipment for residential, commercial, and/or industrial uses, limiting the contribution of thermal energy in terms of consumption of traditional fossil fuel or of thermal energy supplied to the system as a whole just in the start-up phases and/or after possible plant downtime following upon maintenance operations.

iv) Furthermore, apart from the combined process discussed above, namely the use of the reactor SCWO for supplying energy to the reactor SCWG, as likewise for processing the liquid-phase fraction of the reaction products at output from the latter, there may be envisaged other integrations within the process.

For instance, in the case of significant presence of sulphur in the flows of waste fed to the reactor SCWG, and consequent high presence of hydrogen sulphide in the gas produced, it may be convenient, after separation of this component from the gaseous flow of products, to supply also this to the reactor SCWO, within which it can be converted into sulphur oxides, which may be easily treated with operations of sludge depuration that are in themselves well known.

v) The thermal combination between the two processes (supercritical-water oxidation and supercritical-water gasification) is in general always possible to an extent variable according to the type of treated waste, which determines the energies available at the different temperature levels.

vi) The method and plant for waste disposal described herein are moreover well suited as support of the supercritical-water gasification reaction within the reactor SCWG via catalytic devices so as to improve the performance thereof and enable regulation of the composition of the gas produced for the purposes of its introduction into the grid.

vii) The method and plant for disposal (and recovery) of waste described herein are well-suited to an ecologically sustainable valorization of the treated waste both in energy terms with production of flows that can be used for different purposes, amongst which also the production of electrical energy, and in terms of production of flows with high added value (biomethane compatible with the specifications for introduction into the grid). In particular, second-generation biofuel is produced with high energy efficiency of the process and with high yields in terms of recovery and valorization of the waste at input, with minimal and altogether negligible environmental impact, which renders the process as a whole ecologically sustainable.

Of course, the details of construction and the embodiments may vary widely with respect to what has been described and illustrated herein, without thereby departing from the scope of the present invention, as defined in the annexed claims.

For instance, there may be envisaged, according to the needs, different circuit schemes and/or different numbers of components with respect to what has been described and illustrated. For instance, on simpler plants the set of heat exchangers HEX1, HEX2, HEX3 can be reduced to a single heat exchanger HEX 1 (foregoing supply of thermovector fluid THER1IN) or to the ensemble of the heat exchangers HEX1 and HEX2 (safeguarding the possibility of using elsewhere the thermal energy transferred to the thermovector fluid).

Furthermore, it is possible to eliminate all or some of the coolers COOL1-5 (which cool the flow before separation), thus improving the characteristics of the heat exchangers HEX1-HEX5.

The invention claimed is:

1. A plant for the disposal of wastes including:
   a supercritical water oxidation reactor,
   a supercritical water gasification reactor,
   a feeding system configured for feeding at least two organic currents of wastes to said supercritical water oxidation reactor and supercritical water gasification reactor and configured for feeding at least one aqueous current within said plant,
   wherein said feeding system is configured for feeding said at least one aqueous current with a series flow through said supercritical water oxidation reactor and supercritical water gasification reactor and
   wherein said feeding system is furthermore configured for feeding said at least two organic currents of wastes with a parallel flow through said supercritical water oxidation reactor and supercritical water gasification reactor and so as to selectively feed each of said organic currents of wastes to said supercritical water oxidation reactor or to said supercritical water gasification reactor.

2. The plant according to claim 1, wherein said at least one aqueous current includes:
   a first aqueous current including reaction products of said supercritical water gasification reactor, said first aqueous current being fed by said supercritical water gasification reactor to said supercritical water oxidation reactor.

3. The plant according to claim 2, wherein:
   said at least one aqueous current further includes a second aqueous current coming from said supercritical water oxidation reactor, said second aqueous current being fed by said supercritical water oxidation reactor to said supercritical water gasification reactor, and
   said feeding system is furthermore configured to supply a further aqueous current to said supercritical water gasification reactor, wherein said second aqueous current is fed by said feeding system when the further aqueous current fed to said supercritical water gasification reactor has a flow rate which is insufficient with respect to the demand of the supercritical water gasification reactor, so as to restore a demanded flow rate.

4. The plant according to claim 1, wherein the reaction products of said supercritical water gasification reactor flow through a first flow path of a first, a second and a third heat exchanger and are sent to a first liquid/gas separator, said second heat exchanger having a second flow path traversed by a diatermic thermovector fluid.

5. The plant according to claim 4, wherein said first liquid/gas separator is configured for separating the flow of reaction products of said supercritical water oxidation reactor into a liquid phase flow which traverses a first membrane separator and a gas phase flow which is sent to a sulphur scrubber.

6. The plant according to claim 5, wherein said first membrane separator is configured to separate said liquid phase flow into:
a water flow which is sent to said supercritical water gasification reactor by traversing second flow path of said third heat exchanger and said first heat exchanger in order for it to be heated to a supercritical temperature by the flow of reaction products of said supercritical water oxidation reactor which traverses the first flow path of the first and the third heat exchanger, and
in a flow of acid aqueous solution which is sent to a neutralizer.

7. The plant according to claim 6, wherein said neutralizer is configured for neutralizing said flow of acid aqueous solution, in particular by means of a calcium carbonate flow, and it is furthermore configured for feeding the flow of neutralized acid aqueous solution to a splitter which sends a first fraction thereof, containing excess calcium carbonate, to said sulphur scrubber, and a second fraction thereof to a second membrane separator which extracts a pure water flow therefrom and re-circulates the remaining flow towards said neutralizer.

8. The plant according to claim 1, wherein the reaction products of said supercritical water gasification reactor are cooled and sent to a third membrane separator which is configured for separating the flow of said reaction products into a liquid phase fraction and a gaseous phase fraction, wherein the liquid phase fraction constitutes the first aqueous flow which is fed to said supercritical water oxidation reactor, while the gaseous phase fraction is sent to an after-treatment unit.

9. The plant according to claim 8, wherein the liquid phase fraction is fed to a mixing unit configured for mixing said liquid phase fraction with a mixture of one or more of said at least two organic currents of wastes for the delivery to said supercritical water oxidation reactor for the treatment thereof.

10. The plant according to claim 8, wherein said after treatment unit includes a hydrogen sulphide trap, a carbon dioxide trap and an isothermal catalytic reactor configured for the conversion of hydrogen and carbon monoxide into water and methane.

11. The plant according to claim 8, wherein the reaction products of said supercritical water gasification reactor are cooled by flowing through a first cooler, a heat exchanger and a second cooler arranged in series with each other, wherein said heat exchanger is traversed by a diathermic thermovector fluid.

12. A method for the disposal of wastes in a plant for waste disposal including:
a supercritical water oxidation reactor,
a supercritical water gasification reactor,
a feeding system of currents of wastes configured for feeding at least two organic currents of wastes to said supercritical water oxidation reactor and supercritical water gasification reactor and for feeding at least one aqueous current within said plant,
the method comprising the steps of:
feeding, by means of said feeding system, said at least two organics currents of wastes with a parallel flow through said supercritical water oxidation reactor and supercritical water gasification reactor and so as to selectively send each of said organic currents of wastes to said supercritical water oxidation reactor or to said supercritical water gasification reactor,
feeding, by means of said feeding system, said at least one aqueous current with a series flow through said supercritical water gasification reactor and supercritical water oxidation reactor.

13. The method according to claim 12, wherein said at least one aqueous current includes a first aqueous current including reaction products of said supercritical water gasification reactor, said first aqueous current being fed by said supercritical water gasification reactor to said supercritical water oxidation reactor.

14. The method according to claim 13, wherein:
said at least one aqueous current further includes a second aqueous current coming from said supercritical water oxidation reactor, said second aqueous current being fed by said supercritical water oxidation reactor to said supercritical water gasification reactor, and
said feeding system being further configured for feeding a further aqueous current to said supercritical water gasification reactor,
said method further including feeding said second aqueous current, by means of said feeding system, when the further aqueous current fed to said supercritical water gasification reactor has a flow rate which is insufficient with respect to the demand of the supercritical water gasification reactor, so as to restore a demanded value of flow rate.

15. The method according to claim 12, further including cooling the reaction products of said supercritical water oxidation reactor and feeding the cooled reaction products to a first liquid/gas separator configured for separating the flow of reaction products in a liquid phase fraction and a gaseous phase fraction.

16. The method according to claim 15, further comprising sending said liquid phase fraction to a first membrane separator configured for separating said liquid flow into:
a water flow which is recirculated and used for the cooling of reaction products of said supercritical water oxidation reactor in order for it to be heated to supercritical conditions for use in said supercritical water gasification reactor, said water flow comprising said first aqueous current,
a flow of acid aqueous solution that is sent to a neutralizer, and
further comprising sending said gaseous phase fraction to a sulphur scrubber.

17. The method according to claim 12, further including neutralizing said flow of acid aqueous solution in said neutralizer and sending the neutralized acid aqueous solution flow:
in part to a second membrane separator configured for extracting a pure water flow and for re-circulating the remaining flow to said neutralizer, and
in part to said sulphur scrubber.

18. The method according to claim 11, further comprising cooling the reaction products of said supercritical water gasification reactor and sending the cooled reaction products to a liquid/gas separator configured for separating the flow of said reaction products into a liquid phase fraction and a gaseous phase fraction, said liquid phase fraction being said second aqueous current.

19. The method according to claim 18, further including sending said liquid phase fraction towards the inlet of said supercritical water oxidation reactor and sending said gaseous phase fraction towards an after-treatment unit.

\* \* \* \* \*